United States Patent [19]

Shinyama et al.

[11] Patent Number: 5,691,339
[45] Date of Patent: Nov. 25, 1997

[54] CIRCULATORY DISORDER IMPROVING AGENT

[75] Inventors: Hiroshi Shinyama; Toru Kawamura; Minori Okita; Takeshi Uchida; Masahiro Watanabe, all of Hirakata, Japan

[73] Assignee: The Green Cross Corporation, Osaka, Japan

[21] Appl. No.: 424,282

[22] PCT Filed: Aug. 25, 1994

[86] PCT No.: PCT/JP94/01412
§ 371 Date: Apr. 21, 1995
§ 102(e) Date: Apr. 21, 1995

[87] PCT Pub. No.: WO95/05825
PCT Pub. Date: Mar. 2, 1995

[30] Foreign Application Priority Data

Aug. 25, 1993 [JP] Japan .................................. 5-210606
Aug. 25, 1993 [JP] Japan .................................. 5-210668

[51] Int. Cl.$^6$ .................. A61K 31/495; C07D 401/00
[52] U.S. Cl. .................. 514/253; 514/333; 514/334; 514/344; 514/356; 546/257; 546/258; 546/322; 544/360; 544/365
[58] Field of Search .................... 544/360, 365; 546/257, 258, 322; 514/253, 333, 334, 344, 356

[56] References Cited

U.S. PATENT DOCUMENTS 4,886,819 12/1989 Ashimori et al. .................... 514/356
5,462,951 10/1995 Iwao et al. .................... 514/334

OTHER PUBLICATIONS

The Japanese Journal of Pharmacology, vol. 49, Supplementum 1989, 62nd General Meeting, Mar. 25–28, 1989. (Abstract).

The Japanese Journal of Pharmacology, vol. 59, Supplementum 1992, 65th Annual Meeting, Mar. 22–25, 1992. (Abstract).

Clinical and Experimental Pharmacology and Physiology, Blackwell Scientific Publications, vol. 20, No. 2, Feb. 1993, pp. 103–111.

Primary Examiner—Jospeh McKane
Assistant Examiner—Richard S. Myers, Jr.
Attorney, Agent, or Firm—Sughrue, Mion, Zinn, Macpeak & Seas, PLLC

[57] ABSTRACT

A circulatory disorder improving agent comprising, as an active ingredient, a dihydropyridine derivative of the formula (I)

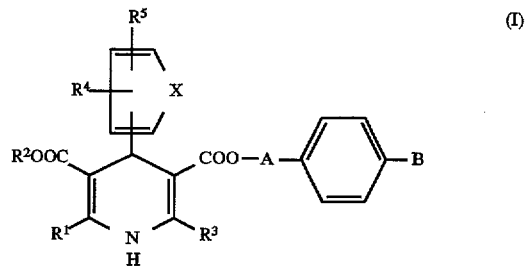

or an acid addition salt thereof. Said circulatory disorder improving agent is particularly useful as an organ circulation disorder improving agent or peripheral circulation improving agent.

8 Claims, No Drawings

CIRCULATORY DISORDER IMPROVING AGENT

This application is a national stage filing under 35 U.S.C. 371 of PCT/JP94/01412, filed Aug. 25, 1994.

TECHNICAL FIELD

The present invention relates to a circulatory disorder improving agent comprising, as an active ingredient, a dihydropyridine derivative having a specific structure or an acid addition salt thereof.

BACKGROUND ART

A dihydropyridine derivative of the formula (I)

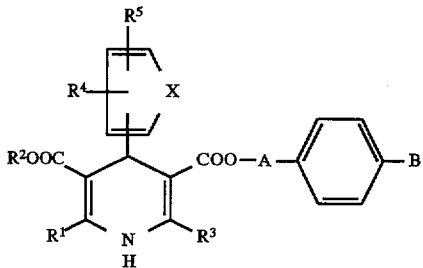

wherein each symbol is as defined later, has a calcium channel antagonistic action and is already known to be useful as an hypotensive agent, a cerebral vasodilating agent and a therapeutic agent for coronary artery disorders (therapeutic agent for angina pectoris) (Japanese Patent Unexamined Publication No. 225356/1988, U.S. Pat. No. 4,886,819, EP-A-257616).

It has been also known that the above-mentioned derivative (I) is extremely useful as a cerebral blood flow increasing agent (Japanese Patent Unexamined Publication No. 62824/1990, EP-A-342577), a therapeutic agent for vasospasm (Japanese Patent Unexamined Publication No. 180826/1990, EP-A-379737) and a heart stimulant (Japanese Patent Unexamined Publication No. 235168/1992, EP-A-463407).

DISCLOSURE OF THE INVENTION

The present inventors have conducted intensive studies of the use of dihydropyridine derivatives (I) and found that the derivatives (I) and acid addition salts thereof have an unexpected action which is completely different from the above-mentioned actions heretofore found, namely, blood flow decrease-suppressive action and blood rheology-, erythrodeformability- and microcirculation-improving action, and that they are useful as organ circulatory disorder improving agents.

In particular, they effectively suppress blood flow decrease in various organs and are useful as organ circulatory disorder improving agents, as well as peripheral circulation improving agents.

Accordingly, the present invention aims at providing circulatory disorder improving agents containing, as an active ingredient, a dihydropyridine derivative (I) or an acid addition salt thereof.

Specifically, the present invention aims at providing an organ circulatory disorder improving agent and a peripheral circulation improving agent.

The present invention relates to a circulatory disorder improving agent comprising, as an active ingredient, a dihydropyridine derivative of the formula

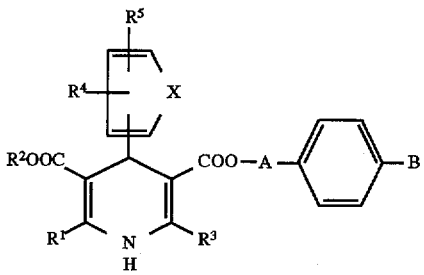

wherein
$R^1$, $R^2$ and $R^3$ are the same or different and each is an alkyl, a cycloalkyl or an alkoxyalkyl;
$R^4$ and $R^5$ are the same or different and each is a hydrogen atom, an alkyl, a cycloalkyl, a halogenated alkyl, an alkylsulfonyl, an alkylsulfinyl, an alkylthio, an alkoxy, a halogensted alkoxy, an alkoxycarbonyl, a cyano, a halogen or a nitro, provided that $R^4$ and $R^5$ are not hydrogen atoms at the same time;
X is a vinylene or —CH=N—;
A is an alkylene; and
B is a group of the formula —N($R^6$)($R^7$) or

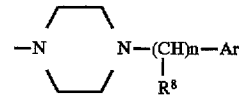

wherein $R^6$, $R^7$ and $R^8$ are the same or different and each is a hydrogen atom, an alkyl, a cycloalkyl, an aralkyl, an aryl or a pyridyl, Ar is an aryl or a pyridyl and n is an integer of 0, 1 or 2 [hereinafter referred to as dihydropyridine derivative (I)] or an acid addition salt thereof (generally a pharmacologically acceptable acid addition salt).

Of the above, a dihydropyridine derivative of the formula (I) wherein $R^1$, $R^2$ and $R^3$ are the same or different and each is an alkyl, $R^4$ is a hydrogen atom, $R^5$ is a nitro, a halogenated alkyl or a cyano, $R^6$ and $R^7$ are the same or different and each is an alkyl, an aralkyl or an aryl, $R^8$ is an aryl, Ar is an aryl and n is 1, is particularly preferable.

The dihydropyridine derivative (I) and an acid addition salt thereof to be used in the present invention are extremely low toxic, and show slow onset of effect and long duration thereof. Accordingly, they are highly effective and highly safe.

The symbols used in the formula (I) in the present specification are explained in the following.

$R^1$, $R^2$ and $R^3$ may be the same or different. The alkyl represented by $R^1$, $R^2$ and $R^3$ may be straight or branched and is preferably a lower alkyl having 1 to 6 carbon atoms, which is exemplified by methyl, ethyl, propyl, isopropyl, butyl, isobutyl, sec-butyl, t-butyl, pentyl, isopentyl, neopentyl and hexyl, with preference given to those having 1 to 4 carbon atoms. The alkyl may have a lower cycloalkylalkyl having 3 to 6 carbon atoms on its terminal, such as cyclopropylmethyl, cyclobutylethyl and cyclopentylmethyl.

As the cycloalkyl represented by $R^1$, $R^2$ and $R^3$, preferred is a lower cycloalkyl having 3 to 6 carbon atoms, such as cyclopropyl, cyclobutyl, cyclopentyl and cyclohexyl.

As the alkoxyalkyl represented by $R^1$, $R^2$ and $R^3$, preferred are those having 3 to 7 carbon atoms, such as methoxyethyl, ethoxyethyl, propoxyethyl, isopropoxyethyl, butoxyethyl, methoxypropyl, 2-methoxy-1-methylethyl and 2-ethoxy-1-methylethyl.

$R^4$ and $R^5$ may be the same or different, and may be substituted at any position on the ring, with preference given to the 2- and/or 3-position relative to the binding site with the dihydropyridine ring.

As the halogen represented by $R^4$ and $R^5$, exemplified are fluorine atom, chlorine atom, bromine atom and iodine atom, and particularly preferred are fluorine atom and chlorine atom.

As the alkyl and the cycloalkyl represented by $R^4$ and $R^5$, preferred are those mentioned for $R^1$ to $R^3$. That is, those which may be straight or branched, and preferably have 1 to 6, more preferably 1 to 4, carbon atoms.

The alkoxy represented by $R^4$ and $R^5$ is preferably a lower alkyl having 1 to 3 carbon atoms, and exemplified by methoxy, ethoxy, propoxy and isopropoxy.

The alkylthio represented by $R^4$ and $R^5$ preferably has 1 to 3 carbon atoms, and is exemplified by methylthio, ethylthio, propylthio and isopropylthio.

As the alkoxycarbonyl represented by $R^4$ and $R^5$, preferred are those having 2 to 4 carbon atoms, such as methoxycarbonyl, ethoxycarbonyl and propoxycarbonyl.

Halogen of the halogenated alkyl or halogenated alkoxy represented by $R^4$ and $R^5$ is exemplified by those mentioned above, and the halogenated alkyl may be that wherein some of the hydrogen atoms are halogenated [e.g., $(CF_3)_2CHCH_2$— and $CF_3CH_2$—] or all of the hydrogen atoms are halogenated, namely, perfluoroalkyl (e.g. trifluoromethyl). Also, the halogenated alkoxy may be that wherein some of the hydrogen atoms are halogenated or all of the hydrogen atoms are halogenated. The halogenated alkyl and halogenated alkoxy respectively have 1 to 6, preferably 1 to 4 carbon atoms.

Examples of the alkyl of alkylsulfonyl and alkylsulfinyl represented by $R^4$ and $R^5$ include those exemplified for $R^1$ to $R^3$ above, namely, those having preferably 1 to 6, more preferably 1 to 4, carbon atoms.

$R^4$ is preferably hydrogen atom and $R^5$ is preferably cyano, nitro or halogenated alkyl (particularly, trifluoromethyl).

$R^6$, $R^7$ and $R^6$ may be the same or different. The alkyl and the cycloalkyl represented by $R^6$, $R^7$ and $R^8$ include those exemplified for $R^1$ to $R^3$.

As the aralkyl represented by $R^6$, $R^7$ and $R^8$, preferred are phenyl $C_1$–$C_3$ alkyl such as benzyl, α-phenylethyl, β-phenylethyl and γ-phenylpropyl.

As the aryl represented by $R^6$, $R^7$ and $R^8$, mention may be made of phenyl or naphthyl.

These aromatic rings (i.e. aralkyl and aryl) may have the same or different substituents at optional positions. The substituents include, for example, those mentioned for $R^4$ and $R^5$ above.

The pyridyl represented by $R^6$, $R^7$ and $R^8$ includes, for example, 2-pyridyl, 3-pyridyl and 4-pyridyl, which may have the same or different substituents mentioned above for $R^4$ and $R^5$.

The alkylene represented by A includes, for example, straight or branched ones having 2 to 4 carbon atoms, which is exemplified by ethylene, trimethylene, tetramethylene and 1,2-dimethylethylene.

The aryl and the pyridyl represented by Ar include, for example, those exemplified for $R^6$, $R^7$ and $R^8$ and may have the same substituents at optional positions, like $R^6$, $R^7$ and $R^8$.

The ring represented by

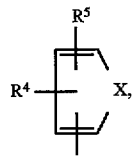

which is the 4-position substituent of dihydropyridine, means a benzene ring when X is vinylene (—CH═CH—); and pyridine when X is —CH═N—. The ring binds to the 4-position of the dihydropyridine at an optional position.

The substituents $R^4$ and $R^5$ may be bonded at any position of ortho-, meta- and para-positions relative to the carbon atom binding to the 4-position of the dihydropyridine, with preference given to the ortho- and/or meta-position(s).

The dihydropyridine derivatives (I) are exemplified by the compounds shown in following Table 1.

TABLE 1

| $R^1$ | $R^2$ | $R^3$ | $R^4$ | $R^5$ | X | A | Ar | $R^8$ | n |
|---|---|---|---|---|---|---|---|---|---|
| Me | Me | Me | H | $NO_2$ | —CH═CH— | ethylene | phenyl | phenyl | 1 |
| Me | Me | Me | H | $NO_2$ | —CH═CH— | ethylene | p-fluorophenyl | phenyl | 1 |
| Me | Me | Me | H | $NO_2$ | —CH═CH— | trimethylene | phenyl | phenyl | 1 |
| Me | Me | Me | H | CN | —CH═N— | ethylene | phenyl | phenyl | 1 |
| Me | Me | Me | H | $CF_3$ | —CH═N— | ethylene | phenyl | phenyl | i |

Note:
Me means methyl.

Preferred dihydropyridine derivatives (I) are 2-[p-(4-benzhydrylpiperazino)phenyl]ethyl methyl 2,6-dimethyl-4-(3-nitrophenyl)-1,4-dihydropyridine-3,5-dicarboxylate, 2-[p-(4-benzhydrylpiperazino)phenyl]ethyl methyl 2,6-dimethyl-4-(4-cyano-2-pyridyl)-1,4-dihydropyridine-3,5-dicarboxylate, and acid addition salts thereof.

The dihydropyridine derivative (I) can be produced by a method known per se.

Specific methods for the production are shown in Japanese Patent Unexamined Publication No. 107975/1988 (U.S. Pat. No. 4,849,429), Japanese Patent Unexamined Publication No. 112580/1988 (U.S. Pat. No. 4,910,195), Japanese Patent Unexamined Publication No. 225386/1988 (U.S. Pat. No. 4,886,819, EP-A-257616), Japanese Patent Unexamined Publication No. 201765/1983 (U.S. Pat. No. 4,892, 875), Japanese Patent Unexamined Publication No. 99042/1988 (U.S. Pat. No. 4,886,819, EP-A-257616), Japanese Patent Unexamined Publication No. 152351/1988 (U.S. Pat. No. 4,910,195) and Japanese Patent Unexamined Publication No. 260064/1986.

The dihydropyridine derivative (I) thus produced can be subjected to known separation and purification steps, such as concentration, extraction, chromatography, reprecipitation and recrystallization, as appropriate, to provide same at an optional purity.

Since the dihydropyridine derivative (I) has a basic group, it can be converted to an acid addition salt by a known method. The salt is subject to no particular limitation as long as it is pharmacologically acceptable. Examples of the salt include salts with inorganic acid, such as hydrochloride, hydrobromide, phosphate and sulfate, and salts with organic acid, such as acetate, succinate, maleate, fumarate, malate and tartrate.

The dihydropyridine derivative (I) and an acid addition salt thereof, which are the active ingredients in the present invention, are useful for the improvement of circulatory disorders in mammals such as mouse, rat, rabbit, dog, cat and human, based on their blood flow decrease-suppressive action and blood rheology-, erythrodeformability- and microcirculation-improving action.

Since they have suppressive action on the decrease of blood flow in various organs, they are useful for the improvement of circulatory disorders in various organs such as brain stem, heart, kidney, adrenal and lung. In addition, they are useful for the prevention and treatment of the diseases induced by peripheral circulation failure in mammals, such as Raynaud's syndrome, arteriosclerosis obliterans, romsoongitis obliterans, Buerger disease, diabetic microvascular disorders and peripheral arterial obstruction (e.g. diabetic gangrene). Moreover, they are useful for the prevention and treatment of hypertension and organ circulatory disorders, as well as for the treatment of cerebrovascular disorders both in acute stages and chronic stages.

When the dihydropyridine derivative (I) or an acid addition salt thereof is used as a circulatory disorder improving agent of the present invention, pharmacologically acceptable additives, such as carrier, excipient and diluent, are mixed as appropriate with pharmaceutically required ingredients, and prepared into pharmaceutical compositions in the form of a powder, granule, tablet, capsule, syrup or injection, which can be administered orally or parenterally.

While the dose of the dihydropyridine derivative (I) or an acid addition salt thereof varies depending on the administration route, symptom, body weight and age of patients, it is preferably administered in an amount of 0.1–100 mg/human/day, preferably 1–20 mg/human/day in one to several times divided doses when orally administering to an adult patient. In the case of intravenous administration, the dihydropyridine derivative (I) or an acid addition salt thereof is preferably administered in an amount of 0.1 to 300 µg/human/day, preferably 5 to 100 µg/human/day in one to several times divided doses a day.

The present invention is described in more detail in the following by illustrative experimental examples, examples and reference examples, to which the invention is not limited.

As regards $^1$H-NMR, used was $CDCl_3$ unless otherwise specified.

The blood rheology improving action of the dihydropyridine derivative (I) and an acid addition salt thereof was tested in Experimental Examples 1 and 2.

The circulatory disorder improving action of the dihydropyridine derivative (I) and an acid addition salt thereof was tested in Experimental Example 3.

Test drugs

Compound of the invention: 2-[p-(4-benzhydrylpiperazino)phenyl]-ethyl methyl 2,6-dimethyl-4-(3-nitrophenyl)-1,4-dihydropyridine-3,5-dicarboxylate •hydrochloride (Compound 2)

Control drugs in Experimental Examples 1 and 2: nilvadipine (NIL) and pentoxifylline (PXF)
Control drugs in Experimental Example 3: nicardipine and hydralazine Test Animals Experimental Examples 1 and 2: Male Stroke-Prone Spontaneously Hypertensive Rat (SHRSP) and male Wistar-Kyoto rat (WKY)
Experimental Example 3: SHRSP

EXPERIMENTAL EXAMPLE 1

Effect on Blood Viscosity and Plasma Viscosity

Test Method

Consecutive daily oral administration of a test drug or a vehicle (solvent) to SHRSP and WKY was started from 9 weeks of age and continued for 3 weeks. Systolic blood pressure and heart rate were measured every week using a programmable sphygmonanometer (BP-98, Softron) before drug administration and 2 hours after the administration.

Determination of Blood Viscosity

After the administration, pentobarbital (40 mg/kg body weight) was intraperitoneally administered, and blood was taken from descendens artery and heparin was added. The blood was immediately used as whole blood. Plasma was obtained by immediately separating the whole blood by centrifugation at 2,000 rpm for 10 minutes and 3,000 rpm for 10 minutes. The viscosity of the whole blood and plasma was determined with a rotary viscometer (E-type viscometer, Tokyo Keiki). The shear rate in the determination was set to 3.84–192.0 $sec^{-1}$ for both the whole blood and the plasma.

Determination of Fibrinogen Concentration

Fresh blood (9 vol) taken from descendens artery and 3.8% sodium citrate (1 vol) were admixed. The plasma obtained by immediate centrifugation at 3,000 rpm for 10 minutes was used as a test sample, and the fibrinogen level was determined by thrombin-clotting time method. Fibrinogen Determination Reagent B was used for the determination.

Results

Using SHRSP, the effect of Compound 2 on blood viscosity after consecutive daily administration thereof for 3 weeks was compared with the effect of nilvadipine (NIL) or pentoxifylline (PXF). A comparison with the effect obtained using normal blood pressure rat (WKY) was done in the same manner, the results of which are summarized in Table 2.

TABLE 2

| Test drug | Dose (mg/kg) | Test animal (n) | Ht (%) | Viscosity (cP) Shear rate ($sec^{-1}$) | | | | | |
|---|---|---|---|---|---|---|---|---|---|
| | | | | 3.84 | 9.60 | 19.2 | 38.4 | 76.8 | 192 |
| SHRSP | | | | | | | | | |
| Vehicle | | (9) | 46.8 ± 0.4 | 11.1 ± 0.9 | 8.7 ± 0.5 | 7.1 ± 0.3 | 5.8 ± 0.2 | 4.9 ± 0.1 | 4.2 ± 0.1 |

TABLE 2-continued

| Test drug | Dose (mg/kg) | Test animal (n) | Ht (%) | Viscosity (cP) Shear rate (sec$^{-1}$) | | | | | |
|---|---|---|---|---|---|---|---|---|---|
| | | | | 3.84 | 9.60 | 19.2 | 38.4 | 76.8 | 192 |
| Compound 2 | 1 | (10) | 46.3 ± 0.4 | 10.1 ± 0.6 | 8.4 ± 0.5 | 7.0 ± 0.2 | 5.6 ± 0.2 | 4.8 ± 0.1 | 4.2 ± 0.1 |
| Compound 2 | 3 | (10) | 45.9 ± 0.3 | 9.5 ± 0.8 | 8.0 ± 0.2 | 6.8 ± 0.1 | 5.4 ± 0.1 | 4.7 ± 0.1 | 4.1 ± 0.0 |
| NIL | 30 | (9) | 45.3 ± 0.3 | 9.9 ± 0.7 | 8.1 ± 0.3 | 6.8 ± 0.2 | 5.5 ± 0.1 | 4.7 ± 0.1 | 4.1 ± 0.1 |
| PXF | 100 | (10) | 46.6 ± 1.1 | 10.5 ± 0.7 | 8.7 ± 0.4 | 7.2 ± 0.3 | 5.7 ± 0.2 | 4.9 ± 0.2 | 4.2 ± 0.1 |
| WKY | | | | | | | | | |
| Vehicle | | (10) | 45.5 ± 0.5 | 9.3 ± 0.6 | 8.3 ± 0.7 | 6.9 ± 0.4 | 5.7 ± 0.3 | 4.9 ± 0.2 | 4.1 ± 0.1 |
| Compound 2 | 3 | (10) | 44.1 ± 0.4* | 9.7 ± 1.0 | 7.4 ± 0.5 | 6.7 ± 0.4 | 5.4 ± 0.2 | 4.7 ± 0.1 | 4.0 ± 0.1 |

Mean ± S.E. Blood viscosity was measured immediately after arterial blood sampling.
*: significant difference from WKY administered with vehicle (P < 0.05)

Effect on Blood Viscosity

No effect of the drug on SHRSP was found in the hematocrit (Ht) value on arterial blood sampling. On the other hand, a significant decrease in Ht value was found in WKY administered with 3 mg/kg body weight of Compound 2 when compared with the group administered with vehicle. Immediately after blood sampling, the whole blood viscosity of the SHRSP group administered with vehicle showed somewhat higher value than the WKY group.

In contrast, the viscosity at respective shear rates decreased dose-dependently by the administration of Compound 2, and the group administered with 3 mg/kg body weight showed almost the same value with the WKY vehicle group. Similarly, the group administered with NIL showed a tendency toward decreased whole blood viscosity, whereas administration of PXF did not cause decrease in the whole blood viscosity.

Likewise, the plasma viscosity of the SHRSP vehicle group showed somewhat higher value than WKY. However, administration of respective drugs had no effect.

Effect on Fibrinogen Concentration

The fibrinogen concentration, which influences the blood viscosity to the greatest degree among the plasma side factors, was measured. The fibrinogen level in the vehicle group was higher in the SHRSP group than in the WKY group, though administration of respective drugs had no effect.

Based on the foregoing results, it is clear that the drug of the present invention had a blood rheology improving effect, as evidenced by the fact that increases in whole blood viscosity observed in the SHRSP vehicle group were suppressed to almost the normal level by consecutive daily administration of Compound 2 for 3 weeks.

EXPERIMENTAL EXAMPLE 2

Effect on Erythrodeformability

Test Method

A test drug or vehicle (solvent) was forcibly administered orally from 9 weeks of age in a dose of 10 ml/kg body weight daily to SHRSP and WKY. Systolic blood pressure and heart rate were measured on the initial day of experiment and 3 weeks after the initiation of the experiment, using a programmable sphygmonanometer (BP-98, Softron). Erythrodeformability was determined 3 weeks after the initiation of the drug administration.

The animals were anesthetized with sodium pentobarbital, and blood was taken from abdominal artery and heparin was added. Using this heparin-added blood, erythrodeformability was immediately determined according to the method of Reid et al [Reid HL et al., J. Clin. Pathol., 29, 855–858 (1976)]. To be specific, the time necessary for physiological saline (control solution) or blood (0.5 ml) to pass through a membrane filter having a pore size of 5 μm (Nucleopore) under 20 cm water column negative pressure was measured. The filter passage time of the blood was corrected (Formula 1) using the filter passage time of the physiological saline, and calculated as a blood volume that passes through per minute (Formula 2). The passage volume was corrected using various Ht values (Formula 3), the result of which was taken as a filter passage rate of erythrocytes and used as an index to show erythrodeformability of the whole blood.

Formula 1:

$$\text{Filter passage time of blood (0.5 ml) (sec, corrected with physiological saline)} = \frac{\text{Average filter passage time of physiological saline (sec)}}{\text{Filter passage time of physiological saline (0.5 ml) (sec)}} \times \text{filter passage time of blood (0.5 ml) (sec)}$$

Formula 2:

$$\frac{\text{Blood passage amount per minute (ml/min)}}{} = \frac{0.5 \text{ ml} \times 60 \text{ sec}}{\text{Value of Formula 1 (sec)}}$$

Formula 3:

$$\frac{\text{Filter passage rate of erythrocytes (ml/min)}}{} = \frac{C_1 \text{ (ml/min)} + C_2 \text{(ml/min)}}{2} \times \frac{Ht}{100}$$

In Formula 3, $C_1$ is the value of Formula 2 obtained using the results of the first determination and $C_2$ is the value of Formula 2 obtained using the results of the second determination.

Results

The effect of consecutive daily administration of Compound 2 for 3 weeks on erythrodeformability was determined according to the method of Reid et al and compared with the results obtained using NIL and PXF as control drugs, the results of which are summarized in Table 3.

TABLE 3

| Drug | Dose (mg/kg) | Sample (n) | Ht (%) | Filterability rate of erythrocytes (ml/min) |
|---|---|---|---|---|
| SHRSP | | | | |
| vehicle | | (12) | 45.5 ± 0.2 | 1.78 ± 0.12 |
| Compound 2 | 1 | (8) | 46.2 ± 0.5 | 2.04 ± 0.09 |
|  | 3 | (8) | 45.9 ± 0.4 | 2.16 ± 0.13* |
| NIL | 30 | (7) | 45.4 ± 0.4 | 2.08 ± 0.11 |
| PXF | 100 | (8) | 47.5 ± 0.2* | 2.15 ± 0.06* |
| WKY | | | | |
| vehicle | | (8) | 43.4 ± 0.5* | 2.15 ± 0.08* |
| Compound 2 | 3 | (8) | 44.6 ± 0.6 | 2.17 ± 0.08* |

Mean ± S.E.
*significant difference from SHRSP administered with vehicle (P < 0.05).

Hematocrit Value

A tendency toward higher hematocrit value than in WKY was found in SHRSP. Ht value significantly increased in SHRSP group administered with PXF (100 mg/kg body weight) in comparison with SHRSP group administered with vehicle. No clear changes in Ht value were caused by the administration of other drugs.

Erythrodeformability

Filterability of erythrocytes immediately after blood sampling significantly decreased in SHRSP administered with vehicle in comparison with WKY group administered with vehicle. Filterability of erythrocytes in SHRSP group was improved dose-dependently by the administration of Compound 2, and the group administered with 3 mg/kg body weight of Compound 2 showed significant improvement in erythrocyte filterability in comparison with the group administered with vehicle. The group administered with NIL (30 mg/kg body weight) also showed improved erythrocyte filterability, and the effect was almost the same as the effect achieved by the group administered with Compound 2. The group administered with PXF (100 mg/kg body weight) showed significant improvement in erythrocyte filterability to almost the same degree achieved by WKY group administered with vehicle. Filterability of erythrocytes in WKY was significantly higher in the group administered with vehicle or Compound 2 (3 mg/kg body weight) than in SHRSP group.

Based on the foregoing results, it is evident that consecutive administration of Compound 2 (1 mg/kg body weight or 3 mg/kg body weight) for 3 weeks resulted in improved erythrodeformability. Accordingly, it is clear that microcirculation improving action was achieved by blood rheological improvements in addition to vasodilating action.

Although the similar effect was obtained by the administration of NIL, NIL required a dose (30 mg/kg body weight) which was 10 times or more greater than the amount of Compound 2. Accordingly, its action is considered to be weaker than the erythrodeformability of Compound 2.

Based on the results of the above experiments, it is evident that dihydropyridine derivative (I) and acid addition salt thereof have microcirculation improving action, which results from blood rheology and erythrodeformability improving effect, and are useful as peripheral circulation improving agents.

EXPERIMENTAL EXAMPLE 3

Effect on Blood Flow Volume in Various Organs and Vascular Resistance

Test Method

SHRSP were bred on a feed containing 4% NaCl (SP feed manufactured by Funabashi Farm, Japan) from 9 weeks to 13 weeks of age to decrease the blood flow volume in various organs of SHRSP. A test drug was orally administered during this period and possible suppression of the decrease in blood flow volume of various organs was examined by the radioactive microsphere method.

Operation Procedure

PF-50 Catheters were respectively inserted into left ventricle of the heart via right common carotid artery and right femoral artery under 1% halothane anesthetization, and the both catheters were dwelled at the posterior region of neck subcutaneously through the back. Insertion of the catheter into left ventricle of the heart was done while monitoring the waveform with a pressure transducer. The blood flow volume in organs was measured after the rats had been left at least for 3 hours after awakening from the anesthetization.

Measurement of Blood Flow Volume in Organs $^{51}$Cr-Labeled radioactive microspheres (100,000, diameter 15.5±0.1 µ, specific activity 1257.3 MBq/g) were injected into left ventricle of the heart over 30 seconds. The microspheres had been dissolved in physiological saline (0.5 ml) containing 0.01% Tween 80 and sonicated at least for 30 minutes to prevent aggregation. The artery blood (control) was taken with a pump manufactured by Harvard Corp. from 5 seconds before microsphere injection, at a rate of 0.458 ml/min for 1 minute. Fifteen minutes after the administration, the animals were slaughtered by an intravenous administration of a lethal dose of pentobarbital solution, and brain, heart, lung, kidney and adrenal were removed and weighed. The radioactivity of the microsphere solution to be injected, control blood and tissue sample was measured with a γ-counter.

The blood flow volume in organs was calculated by the following formula.

Organ blood flow volume=[radioactivity of organ (CPM) /radioactivity of control blood (CPM)×0.458 (ml/min)]/ weight of organ (g)

Note that injected radioactivity was taken as the total radioactivity before injection minus the residual radioactivity in the injector after injection, and organ blood flow volume was expressed as the blood flow volume per g of tissue.

Results

Changes in blood flow volume in various organs of SHRSP caused by the administration of test drugs are summarized in Table 4.

TABLE 4

|  | 9 weeks old Control (9) | 13 weeks old | | | |
|---|---|---|---|---|---|
|  | | Control (9) | Compound 2 1 mg/kg (8) | Nicardipine 10 mg/kg (8) | Hydralazine 3 mg/kg (8) |
| organ | | | | | |
| cerebrum | 1.568 ± 0.214 | 1.375 ± 0.127 | 1.571 ± 0.139 | 1.339 ± 0.142 | 1.454 ± 0.185 |
| cerebellum | 1.261 ± 0.119 | 1.084 ± 0.096 | 1.421 ± 0.077* | 1.155 ± 0.095 | 1.355 ± 0.118 |
| brain stem | 1.111 ± 0.110 | 0.810 ± 0.064 | 1.060 ± 0.069* | 0.931 ± 0.104 | 0.853 ± 0.066 |
| heart | 8.238 ± 0.772 | 6.358 ± 0.375 | 6.988 ± 0.459 | 6.145 ± 0.381# | 7.226 ± 0.562 |
| lung | 0.279 ± 0.027 | 0.266 ± 0.088 | 0.377 ± 0.120 | 0.155 ± 0.039# | 0.216 ± 0.040 |
| kidney | 5.839 ± 0.603 | 3.382 ± 0.255 | 6.876 ± 0.629*** | 5.429 ± 0.497** | 5.931 ± 0.481*** |
| adrenal | 3.620 ± 0.489 | 2.256 ± 0.187 | 3.359 ± 0.499* | 3.491 ± 0.346** | 2.586 ± 0.271 |

Each value is various organ blood flow (ml/g) per minute expressed in mean ± S.E. relative to organ weight.
: significant difference from the value of SHRSP at 9 weeks of age
*: significant difference from the value of SHRSP (13 weeks old) showing no onset of disease (*: P < 0.05, : P < 0.01, *: P < 0.001) Figures in parentheses are numbers of test animals. A test drug was orally administered from 9 weeks of age to 13 weeks of age.

With regard to the blood flow volume in various organs, the group administered with Compound 2 showed a significant increase in cerebellum, brain stem, kidney and adrenal, in comparison with the results obtained from 13 weeks old rats showing no onset of disease, as well as a tendency to increase in cerebrum. Every organ blood flow volume showed no difference from the value of 9 weeks old rats at the initiation of the drug administration, thus completely suppressing blood flow decrease due to vascular disorders.

The group administered with nicardipine showed significant decrease in blood flow volume, in comparison with the value of 9 weeks old rats with regard to heart and lung. The blood flow volume in kidney and adrenal showed significant increase from the value of 13 weeks old rats. The group administered with hydralazine showed significant blood flow volume increase only in kidney, in comparison with the value of 13 weeks old rats.

Vascular resistance of each organ significantly decreased in cerebellum, brain stem and kidney in the group administered with Compound 2, in comparison with the value of 13 weeks old rats showing no onset of disease, and showed a tendency to decrease also in cerebrum and adrenal.

The group administered with nicardipine showed significant increase, in comparison with the value of 9 weeks old rats with regard to brain stem, heart and lung, as well as significant decrease only in kidney and adrenal, in comparison with the value of 13 weeks old rats showing no onset of disease. The group administered with hydralazine showed significant increase in brain stem and adrenal, in comparison with the value of 9 weeks old rats, and significant decrease only in kidney, in comparison with the value of 13 weeks old rats showing no onset of disease.

It has been made clear that consecutive daily oral administration of Compound 2 to SHRSP from 9 weeks to 13 weeks of age resulted in retention of various organ blood flow volume of SHRSP at 9 weeks of age (at initiation of drug administration) in all organs measured. In this case, there was found no difference in blood pressure at the time of blood flow volume determination among the groups treated with 3 kinds of drugs. However, Compound 2 showed stronger suppression of blood flow decrease, in comparison with other 2 drugs.

Based on the experimental results as described, it is evident that dihydropyridine derivative (I) and acid addition salt thereof suppress decrease in various organ blood flow volumes, which is associated with hypertension found in SHRSP, namely, manifestation of organ vascular disorders, and are useful as organ circulatory disorder improving agents.

REFERENCE EXAMPLE

Synthesis of 2-[p-(4-benzhydrylpiperazino)phenyl]ethyl methyl-2,6-dimethyl-4-(3-nitrophenyl)-1,4-dihydropyridine-3,5-dicarboxylate (Compound 1) and hydrochloride thereof (Compound 2)

3-Nitrobenzaldehyde (1.144 g, 7.57 mmol), [p-(4-benzhydrylpiperazino)phenyl]ethyl acetoacetate (3.464 g, 7.59 mmol) and methyl 3-aminocrotonate (873 mg, 7.58 mmol) were placed in a 100 ml eggplant flask, and isopropanol (12 ml) was added. The flask was equipped with a Dimroth condenser and the mixture was refluxed under heating for 16 hours. The reaction solvent was distilled away under reduced pressure and the residue was separated by column chromatography [silica gel, chloroform: methanol (45:1)] and column chromatography [silica gel, ethyl acetate:n-hexane (2:3)], and the crude product obtained was purified by high performance liquid chromatography to give 2.503 g of the title Compound 1 (yield 48%).

IR$v_{max}^{KBr}$ cm$^{-1}$: 1680, 1520
$^1$H-NMRδ:8.06 (1H, t, J=2 Hz), 7.97 (1H, ddd, J=8; 2; 1 Hz), 7.1–7.6 (12H), 7.03 (2H, d, J=8.6 Hz), 6.80 (2H, d, J=8.6 Hz), 6.02 (1H, s), 5.07 (1H, s), 4.26 (1H, s), 4.22 (2H, t, J=7 Hz), 3.64 (3H, s), 3.15 (4H, dd, J=5; 4.7 Hz), 2.81 (2H, t, J=7 Hz), 2.55 (4H, dd, J=5; 4.7 Hz), 2.33, 2.28 (3H, s respectively)

The Compound 1 (2.124 g, 3.16 mmol) was placed in a 200 ml-eggplant flask and the flask was rubber-sealed. Methylene chloride (100 ml) was added thereto, and after dissolution of the content, the mixture was stirred at room temperature for 30 minutes while introducing hydrogen chloride gas. The resultant crystals were collected by filtration to give about 2.22 g of the title Compound 2.

IR$v_{max}^{KBr}$ cm$^{-1}$: 2450, 1680, 1525, 1350. $^1$H-NMRδ: 13.72 (1H, brs), 8.05–7.9 (6H), 7.82, 7.26 (4H, A$_2$B q, J=8.6 Hz), 7.6–7.3 (8H), 6.28 (1H, s), 5.2–5.05 (2H), 5.01 (2H, s), 4.27 (2H, t, J=6.5 Hz), 4.3–4.1 (2H), 3.66 (3H, s), 3.65–3.45 (4H), 2.95 (2H, t, J=6.5 Hz), 2.36, 2.33 (3H, s respectively)

EXAMPLE 1

Tablet

| (1) Compound 2 | 10 g |
|---|---|
| (2) Fine granule No. 209 for direct compression (manufactured by Fuji Kagakusha) | 110 g |

13

-continued

| | | |
|---|---|---|
| | Magnesium aluminate metasilicate | 20% |
| | Corn starch | 30% |
| | Lactose | 50% |
| (3) | Crystalline cellulose | 60 g |
| (4) | CMC calcium | 18 g |
| (5) | Magnesium stearate | 2 g |

(1), (3) and (4) were passed through a 100 mesh-sieve in advance. (1), (3), (4) and (2) were respectively dried to a certain water content, after which the ingredients were mixed at the above weight ratio by a mixing machine. (5) was added to the homogeneously-mixed powder and was mixed for a short time (30 seconds). The mixed powder was compressed into tablets of 200 mg each.

The tablets may be gastro-coated using a film coating agent such as polyvinyl acetal diethylaminoacetate or coated with a food coloring.

EXAMPLE 2

Capsule

| | | |
|---|---|---|
| (1) | Compound 2 | 50 g |
| (2) | Lactose | 930 g |
| (3) | Magnesium stearate | 20 g |

The above ingredients were weighed and homogeneously mixed, after which the mixed powder was charged in hard gelatin capsules at 200 mg each.

EXAMPLE 3

Injection

| | | |
|---|---|---|
| (1) | Compound 2 | 5 mg |
| (2) | Glucose | 100 mg |
| (3) | Physiological saline | 10 ml |

The mixed solution of the above was filtered through a membrane filter, after which it was sterilized by filtration. The filtrate was aseptically poured into a vial, charged with a nitrogen gas and sealed to afford an intravenous injection.

EXAMPLE 4

Compound 2 (20.1 g) was added to a mixture (650 g) of unsaturated fatty acid monoglyceride (Excel 0–95R, manufactured by Kao Corp.) and polyoxyethylenesorbitan monooleate (T0–10M, manufactured by Nikko Chemical Corp.) (1:1), and dissolved and stirred at 40° C. to give a non-micell solution. The obtained solution (600 g) and magnesium aluminate metasilicate (370 g, Neusilin US$_2$, manufactured by Fuji Kagaku Sangyo) were mixed in a rotary granulator. Then, Carmellose sodium A (30 g) was mixed and stirred, and purified water (250 ml) was added for granulation. The granules were dried at 40° C. for 17 hours with a forced-air drier, passed through a 42–200 mesh-sieve to prepare 550 g of granules to be packed in capsules.

Industrial Applicability

A pharmaceutical composition comprising, as an active ingredient, a dihydropyridine derivative (I) or an acid addition salt thereof of the present invention is useful as a circulatory disorder improving agent. In particular, the composition is useful as an organ circulatory disorder improving agent and peripheral circulation improving agent.

What is claimed is:

1. A method for treating disease induced by an increase in blood viscosity or decrease in filterability of erythrocyte in peripheral circulation comprising administering a pharmaceutically effective amount of a dihydropyridine derivative of the formula (I)

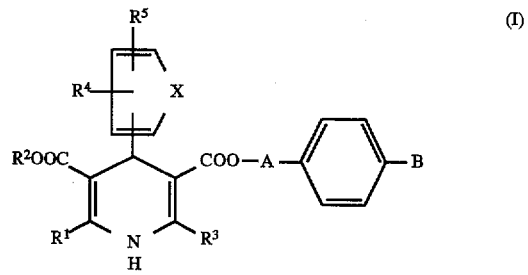

wherein
$R^1$, $R^2$ and $R^3$ are the same or different and each is an alkyl having 1–6 carbon atoms, a cycloalkyl having 3–6 carbon atoms or an alkoxyalkyl;
$R^4$ and $R^5$ are the same or different and each is a hydrogen atom, an alkyl having 1–6 carbon atoms, a cycloalkyl having 3–6 carbon atoms, a halogenated alkyl, an alkylsulfonyl, an alkylsulfinyl, an alkylthio, an alkoxy, a halogenated alkoxy, an alkoxycarbonyl, a cyano, a halogen or a nitro, provided that $R^4$ and $R^5$ are not hydrogen atoms at the same time;
X is a vinylene or —CH=N—;
A is a alkylene; and
B is a group of the formula —N($R^6$) ($R^7$) or

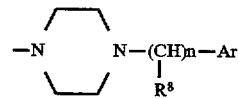

wherein $R^6$, $R^7$ and $R^8$ are the same or different and each is a hydrogen atom, an alkyl having 1–6 carbon atoms, a cycloalkyl having 3–6 carbon atoms, a phenyl $C_1$–$C_3$ alkyl, a phenyl, a naphthyl, or a pyridyl, Ar is a phenyl, a naphthyl or a pyridyl and n is an integer of 0, 1 or 2 or an acid addition salt thereof; and a pharmaceutically acceptable carrier.

2. A method for improving blood rheology comprising administering a pharmaceutically effective amount of a dihydropyridine derivative of the formula (I)

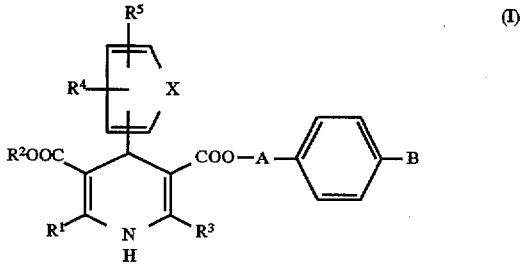

wherein
$R^1$, $R^2$ and $R^3$ are the same or different and each is an alkyl having 1–6 carbon atoms, a cycloalkyl having 3–6 carbon atoms or an alkoxyalkyl;
$R^4$ and $R^5$ are the same or different and each is a hydrogen atom, an alkyl having 1–6 carbon atoms, a cycloalkyl having 3–6 carbon atoms, a halogenated alkyl, an alkylsulfonyl, an alkylsulfinyl, an alkylthio, an alkoxy, a halogenated alkoxy, an alkoxycarbonyl, a cyano, a halogen or a nitro, provided that $R^4$ and $R^5$ are not hydrogen atoms at the same time;

X is a vinylene or —CH=N—;
A is a alkylene; and
B is a group of the formula —N($R^6$) ($R^7$) or

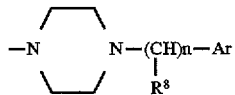

wherein $R^6$, $R^7$ and $R^8$ are the same or different and each is a hydrogen atom, an alkyl having 1–6 carbon atoms, a cycloalkyl having 3–6 carbon atoms, a phenyl $C_1$–$C_3$ alkyl, a phenyl, a naphthyl, or a pyridyl, Ar is a phenyl, a naphthyl or a pyridyl and n is an integer of 0, 1 or 2 or an acid addition salt thereof; and a pharmaceutically acceptable carrier.

3. A method for improving erythrodeformability comprising administering a pharmaceutically effective amount of a dihydropyridine derivative of the formula (I)

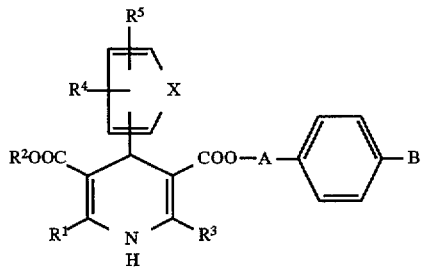

wherein
$R^1$, $R^2$ and $R^3$ are the same or different and each is an alkyl having 1–6 carbon atoms, a cycloalkyl having 3–6 carbon atoms or an alkoxyalkyl;
$R^4$ and $R^5$ are the same or different and each is a hydrogen atom, an alkyl having 1–6 carbon atoms, a cycloalkyl having 3–6 carbon atoms, a halogenated alkyl, an alkylsulfonyl, an alkylsulfinyl, an alkylthio, an alkoxy, a halogenated alkoxy, an alkoxycarbonyl, a cyano, a halogen or a nitro, provided that $R^4$ and $R^5$ are not hydrogen atoms at the same time;
X is a vinylene or —CH=N—;
A is a alkylene; and
B is a group of the formula —N ($R^6$) ($R^7$) or

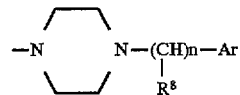

wherein $R^6$, $R^7$ and $R^8$ are the same or different and each is a hydrogen atom, an alkyl having 1–6 carbon atoms, a cycloalkyl having 3–6 carbon atoms, a phenyl $C_1$–$C_3$ alkyl, a phenyl, a naphthyl, a pyridyl, Ar is a phenyl, a naphthyl, or a pyridyl and n is an integer of 0, 1 or 2 or an acid addition salt thereof; and a pharmaceutically acceptable carrier.

4. The method of any one of claims 1–3 comprising orally administering said dihydropyridine derivative or the acid addition salt thereof in a dose of 0.1–100 mg/human/day.

5. The method of any one of claims 1–3 comprising intravenously administering said dihydropyridine derivative or the acid addition salt thereof in a dose of 0.1 to 300 μg/human/day.

6. The method of any one of claims 1–3 wherein said $R^1$, $R^2$ and $R^3$ are the same or different and each is an $C_1$–$C_6$ alkyl, said $R^4$ is a hydrogen atom, said $R^5$ is a nitro, a halogenated $C_1$–$C_6$ alkyl or a cyano, said $R^6$ and $R^7$ are the same or different and each is an $C_1$–$C_6$ alkyl, a phenyl $C_1$–$C_3$ alkyl, a phenyl, or a naphthyl, said $R^8$ is a phenyl or a naphthyl, and said n is 1, or an acid addition salt thereof.

7. The method of any one of claims 1–3 wherein said dihydropyridine derivative or the acid addition salt thereof is orally administered in a dose of 0.1–100 mg/human/day; and said $R^1$, $R^2$ and $R^3$ are the same or different and each is an $C_1$–$C_6$ alkyl, said $R^4$ is a hydrogen atom, said $R^5$ is a nitro, a halogenated $C_1$–$C_6$ alkyl or a cyano, said $R^6$ and $R^7$ are the same or different and each is an $C_1$–$C_6$ alkyl, a phenyl $C_1$–$C_3$ alkyl, a phenyl, or a naphthyl, said $R^8$ is a phenyl or a naphthyl, and said n is 1, or an acid addition salt thereof.

8. The method of any one of claims 1–3 wherein said dihydropyridine derivative or the acid addition salt thereof is intravenously administered in a dose of 0.1 to 300 μg/human/day; and
said $R^1$, $R^2$ and $R^3$ are the same or different and each is an $C_1$–$C_6$ alkyl, said $R^4$ is a hydrogen atom, said $R^5$ is a nitro, a halogenated $C_1$–$C_6$ alkyl or a cyano, said $R^6$ and $R^7$ are the same or different and each is an $C_1$–$C_6$ alkyl, a phenyl $C_1$–$C_3$ alkyl, a phenyl or a naphthyl, said $R^8$ is a phenyl or a naphthyl, and said n is 1, or an acid addition salt thereof.

* * * * *